United States Patent [19]
Jaen et al.

[11] Patent Number: 5,089,497
[45] Date of Patent: Feb. 18, 1992

[54] SUBSTITUTED PIPERAZINES AS CENTRAL NERVOUS SYSTEM AGENTS

[75] Inventors: Juan C. Jaen, Plymouth; David G. Nickell, Ann Arbor; Donna M. Reynolds, Plymouth; Sarah J. Smith, Ann Arbor; Lawrence D. Wise, Ann Arbor; David J. Wustrow, Ann Arbor, all of Mich.

[73] Assignee: Warner-Lambert Company, Morris Plains, N.J.

[21] Appl. No.: 585,742

[22] Filed: Sep. 20, 1990

[51] Int. Cl.$^5$ .................. A61K 31/495; C07D 403/00; C07D 401/00; C07D 241/02
[52] U.S. Cl. .................. 514/253; 514/252; 544/295; 544/357; 544/360; 544/363; 544/364
[58] Field of Search .............. 544/295, 357, 360, 364; 514/252, 253

[56] References Cited

U.S. PATENT DOCUMENTS

| | | | |
|---|---|---|---|
| 3,177,219 | 4/1965 | Brossi et al. | 514/252 |
| 3,362,956 | 1/1968 | Archer | 514/252 |
| 4,515,793 | 5/1985 | Werbel et al. | 514/252 |

FOREIGN PATENT DOCUMENTS 452530 10/1976 Spain.
1551993 9/1976 United Kingdom.

OTHER PUBLICATIONS

J. R. Boissier et al., CA63-15381g (1965).
Societe Industrielle pour la Fabrication des Antibiotques, CA59-2832e.
Societe Industrielle pour la Fabrication des Antibiotiques, CA 59-11521a.
Chemical Pharmaceutical Bulletin, vol. 26, pp. 3296-3305 (1978) M. Sato, et al.
JP 4804478 (62436U-B) Daiichi Seiyaku Co. Ltd.
Boll. Chem. Farm. vol. 119, pp. 608-618 (1980), C. Bacciarelli et al.

*Primary Examiner*—Cecilia Shen
*Attorney, Agent, or Firm*—Francis J. Tinney

[57] ABSTRACT

Substituted piperazines and derivatives thereof are described, as well as methods for the preparation and pharmaceutical composition of same, which are useful as central nervous system agents and are particularly useful as dopaminergic, antipsychotic, and antihypertensive agents as well as for treating hyperprolactinaemia-related conditions and central nervous system disorders.

7 Claims, No Drawings

SUBSTITUTED PIPERAZINES AS CENTRAL NERVOUS SYSTEM AGENTS

BACKGROUND OF THE INVENTION

The present invention relates to novel substituted piperazines and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents.

A series of 1-pyridinyl-1-butanones, 1-indolyl-1-butanones, and related compounds were synthesized by Sato, M., et al, *Chemical Pharmaceutical Bulletin*, Volume 26, pages 3296–3305 (1978) as potential psychotropic agents.

A series of piperazinylbutane derivatives useful as depressants for the central nervous system is disclosed in JP 48004478.

A series of 1-phenyl-4-pyridylethyl-piperazines possessing tranquilizing and appetite depressant properties and also an effect on blood pressure is disclosed in U.S. Pat. No. 3,177,219.

A series of 1-pyridylalkyl-4-phenylpiperazines were synthesized by Bacciarelli, C., et al, *Boll. Chem. Farm*, Volume 119, pages 608–618 (1980) as hypotensive, antihistaminic and adrenolytic agents.

A series of 1-alkyl-4-arylpiperazines is disclosed in ES 452530.

A series of substituted 1-alkyl-4-phenylpiperazines is disclosed in United Kingdom Patent 1,551,993.

A series of phenyl piperazines useful in the treatment of a schistosomiasis is disclosed in U.S. Pat. No. 4,515,793.

A series of 1-[(heterocyclyl)-lower-alkyl]-4-substituted-piperazines useful as depressants on the autonomic nervous system, the cardiovascular system, and the skeletal muscular system is disclosed in U.S. Pat. No. 3,362,956.

However, the compounds disclosed in the aforementioned references do not disclose or suggest the combination of structural variations of the compounds of the present invention described hereinafter.

SUMMARY OF THE INVENTION

Accordingly, the present invention is a compound of Formula I

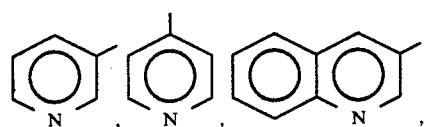

wherein R is

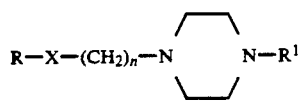

or

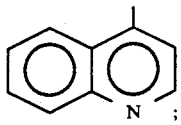

X is

or —CH$_2$—;

n is an integer of 2 to 4;

R$^1$ is 2- or 3-1H-indolyl, or 2- or 3-1H-indolyl substituted by lower alkyl, lower alkoxy, or halogen, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl, or 2- or 3-thienyl substituted by lower alkyl or halogen, 2- or 3-furanyl, or 2- or 3-furanyl substituted by lower alkyl or halogen, 2-, 4-, or 5-thiazolyl, or 2-, 4-, or 5-thiazolyl substituted by lower alkyl or halogen; or a pharmaceutically acceptable acid addition salt thereof.

As dopaminergic agents, the compounds of Formula I are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

"Lower alkoxy" is O-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium and the like.

"Noble metal" is platinum, palladium, rhodium, ruthenium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred compound of Formula I is one wherein $R^1$ is 2- or 3-1H-indolyl, or 2- or 3-1H-indolyl substituted by lower alkyl, lower alkoxy, or halogen, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-, or 3-thienyl or 2- or 3-thienyl substituted by lower alkyl or halogen.

Another preferred embodiment is a compound of Formula I wherein $R^1$ is 2- or 3-1H-indolyl, 2-, 3-, or 4-pyridinyl, 2-, 4-, or 5-pyrimidinyl, or 2- or 3-thienyl.

Particularly valuable are:
1-(3-Pyridinyl)-4-[4-(2-pyridinyl)-1-(piperazinyl)]-1-butanone;
1-(2-Pyridinyl)-4-[4-(3-pyridinyl)butyl]piperazine;
1-(4-Pyridinyl)-4-[4-(2-pyridinyl)-1-piperazinyl]-1-butanone;
2-[4-[4-(4-Pyridinyl)butyl]-1-piperazinyl]pyridine;
2-[4-[4-(4-Pyridinyl)butyl]-1-piperazinyl]pyrimidine;
1-(2-Pyridinyl)-4-[3-(3-pyridinyl)propyl]piperazine;
1-(3-Quinolinyl)-4-[4-(2-pyridinyl)-1-(piperazinyl)]-1-butanone;
3-[4-[4-(2-Pyridinyl)-1-piperazinyl]butyl]quinoline;
3-[4-[4-(2-Pyrimidinyl)-1-piperazinyl]butyl]quinoline;
1-(4-Quinolinyl)-4-[4-(2-pyridinyl)-1-piperazinyl]-1-butanone;
1-(3-Pyridinyl)-4-[4-(2-pyrimidinyl)-1-piperazinyl]-1-butanone;
1-(4-Pyridinyl)-4-[4-(2-pyrimidinyl)-1-piperazinyl]-1-butanone; and
4-[4-[4-(2-Pyridinyl)-1-piperazinyl]butyl]quinoline;
or a pharmaceutically acceptable acid addition salt thereof.

The compounds of Formula I are valuable dopaminergic agents. The tests employed indicate that compounds of Formula I possess dopaminergic activity. Thus, the compounds of Formula I were tested for their ability to inhibit locomotor activity in mice according to the assay described by J. R. McLean, et al, *Pharmacology, Biochemistry and Behavior*, Volume 8, pages 97–99 (1978); for their ability to inhibit [$^3$H]spiroperidol binding in a receptor assay described by D. Grigoriadis and P. Seeman, *Journal of Neurochemistry*, Volume 44, pages 1925–1935 (1985); and for their ability to inhibit dopamine synthesis in rats according to the protocol described by J. R. Walters and R. H. Roth, *Naunyn-Schmiedeberg's Archives of Pharmacology*, Volume 296, pages 5–14 (1976). The above test methods are incorporated herein by reference. The data in the table show the dopaminergic activity of representative compounds of Formula I.

TABLE 1

| | Biological Activity of Compounds of Formula 1 | | | |
|---|---|---|---|---|
| Example Number | Compound | Inhibition of Locomotor Activity in Mice ED$_{50}$, mg/kg, IP | % Reversal of Brain Dopamine Synthesis in Rats at 10 mg/kg, IP | Inhibition of [$^3$H]Spiroperidol Binding IC$_{50}$, μM |
| 2 | 1-(3-Pyridinyl)-4-[4-(2-pyridinyl)-1-(piperazinyl)]-1-butanone | 6.3 | 43 | 2.87 |
| 8 | 1-(2-Pyridinyl)-4-[4-(2-pyridinyl)butyl]piperazine | 2.7 | 67 | — |
| 4 | 1-(4-Pyridinyl)-4-[4-(2-pyridinyl)-1-piperazinyl]-1-butanone | 7.6 | 35 | 2.13 |
| 9 | 2-[4-[4-(4-Pyridinyl)butyl]-1-piperazinyl]pyridine | 4.0 | 79 | 0.835 |
| 10 | 2-[4-[4-(4-Pyridinyl)butyl]-1-piperazinyl]pyrimidine | 10.1 | 35 | 4.18 |
| 1 | 1-(2-Pyridinyl)-4-[3-(3-pyridinyl)propyl]piperazine | 3.1 | — | — |
| 6 | 1-(3-Quinolinyl)-4-[4-(2-pyridinyl)-1-(piperazinyl)]-1-butanone | 2.8 | — | 0.486 |
| 11 | 3-[4-[4-(2-Pyridinyl)-1-piperazinyl]butyl]quinoline | 2.2 | 100 | 0.155 |
| 12 | 3-[4-[4-(2-Pyrimidinyl)-1-piperazinyl]butyl]quinoline | 1.2 | — | — |
| 7 | 1-(4-Quinolinyl)-4-[4-(2-pyridinyl)-1-piperazinyl]-1-butanone | 13 | — | — |

TABLE 1-continued

| | | Biological Activity of Compounds of Formula 1 | | |
| --- | --- | --- | --- | --- |
| Example Number | Compound | Inhibition of Locomotor Activity in Mice $ED_{50}$, mg/kg, IP | % Reversal of Brain Dopamine Synthesis in Rats at 10 mg/kg, IP | Inhibition of [$^3$H]Spiroperidol Binding $IC_{50}$, µM |
| 13 | 4-[4-[4-(2-Pyridinyl)-1-piperazinyl]-butyl]quinoline | 3.2 | — | 0.279 |

A compound of Formula Ia

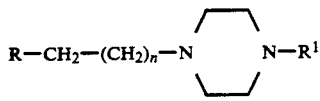

Ia wherein R is

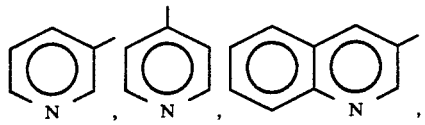

or

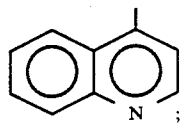

n is an integer of 2 to 4;

$R^1$ is 2- or 3-1H-indolyl, or 2- or 3-1H-indolyl substituted by lower alkyl, lower alkoxy, or halogen, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl, or 2- or 3-thienyl substituted by lower alkyl or halogen, 2- or 3-furanyl, or 2- or 3-furanyl substituted by lower alkyl or halogen, 2-, 4-, or 5-thiazolyl, or 2-, 4-, or 5-thiazolyl substituted by lower alkyl or halogen; or a pharmaceutically acceptable acid addition salt thereof may be prepared by reacting a compound of Formula Ib

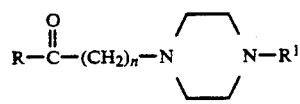

Ib wherein R, $R^1$, and n are as defined above with a reducing agent such as, for example, hydrazine, in the presence of an alkaline catalyst such as sodium hydroxide, potassium hydroxide, sodium methoxide, sodium ethoxide and the like, and a solvent such as, for example, ethylene glycol and the like, or amalgamated zinc and an acid such as, for example, concentrated hydrochloric acid and the like optionally in the presence of a solvent such as, for example, ethanol, acetic acid, dioxane, toluene and the like, or treating a compound of Formula Ib with hydrogen in the presence of a catalyst such as a noble metal, for example, palladium on charcoal in the presence of a solvent such as, for example, ethanol and the like to give a compound of Formula Ia. Preferably, the reaction is carried out with hydrazine in the presence of potassium hydroxide and ethylene glycol.

Alternatively, a compound of Formula Ia may be prepared from a compound of Formula II

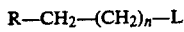

II wherein L is a halogen, or a leaving group such as, for example, methanesulfonyloxy, toluenesulfonyloxy and the like, and R and n are as defined above, and a compound of Formula III

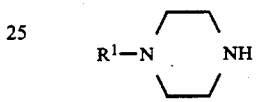

III wherein $R^1$ is as defined above in the presence of a base such as, for example, an alkali metal or alkaline earth metal hydroxide, carbonate or bicarbonate, for example, sodium hydroxide, sodium carbonate, sodium bicarbonate, potassium hydroxide, potassium carbonate, potassium bicarbonate and the like in the presence of a solvent such as, for example, acetonitrile and the like to give a compound of Formula Ia. Preferably, the reaction is carried out in the presence of potassium bicarbonate and acetonitrile.

A compound of Formula Ib is prepared from a compound of Formula IV

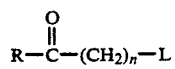

IV wherein R, n, and L are as defined above and a compound of Formula III using the methodology used to prepare a compound of Formula Ia from a compound of Formula II and a compound of Formula III.

Compounds of Formula II, Formula III, and Formula IV are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

1-(2-Pyridinyl)-4-[3-(3-pyridinyl)propyl]piperazine

A solution of 3-pyridinylpropylchloride (Example A) (3.0 g, 0.0193 mol), 1-(2-pyridinyl)piperazine (3.15 g, 0.0193 mol), potassium iodide (0.8 g, 0.005 mol) is dissolved in N,N-dimethylformamide (80 mL) and heated to 80° C. for 12 hours. The reaction is cooled and the precipitate is filtered. The filtrate is washed with sodium carbonate and extracted with dichloromethane. The organic layer is evaporated in vacuo and the residue is purified by column chromatography (silica gel, 10% ethanol/ethyl acetate). The major product is taken up in diethyl ether and the precipitate is filtered. The filtrate is evaporated in vacuo to give 0.8 g of 1-(2-pyridinyl)-4-[3-(3-pyridinyl)propyl]piperazine as a white solid; mp 51–52° C.

EXAMPLE 2

1-(3-Pyridinyl)-4-[4-(2-pyridinyl)-1-piperazinyl]-1-butanone

A solution of 4-chloro-1-(3-pyridinyl)-1-butanone (Example B) (9 g, 0.049 mol), 1-(2-pyridinyl)piperazine (24 g, 0.147 mol), and potassium iodide (0.8 g, 0.005 mol) is heated to 120° C. for 5 minutes. The residue is taken up in chloroform (40 mL) and the precipitate is filtered. The filtrate is evaporated in vacuo and purified by column chromatography (silica gel, 2% methanol/dichloromethane). The major product is crystallized from 2-propanol/diethyl ether to give 6.7 g 1-(3-pyridinyl)-4-[4-(2-pyridinyl)-1-piperazinyl]-1-butanone as a white solid; mp 89° C.

In a process analogous to Example 2 using appropriate starting materials the corresponding compounds of Formula I (Examples 3 to 7) are prepared as follows:

EXAMPLE 3

1-(3-Pyridinyl)-4-[4-(2-pyrimidinyl)-1-piperazinyl]-1-butanone mp 109–112° C.

EXAMPLE 4

1-(4-Pyridinyl)-4-[4-(2-pyridinyl)-1-piperazinyl]-1-butanone mp 89° C.

EXAMPLE 5

1-(4-Pyridinyl)-4-[4-(2-pyrimidinyl)-1-piperazinyl]-1-butanone mp 100° C.

EXAMPLE 6

1-(3-Quinolinyl)-4-[4-(2-pyridinyl)-1-(piperazinyl)]-1-butanone mp 96-97° C.

EXAMPLE 7

1-(4-Quinolinyl)-4-[4-(2-pyridinyl)-1-piperazinyl]-1-butanone mp 198-199° C.

EXAMPLE 8

1-(2-Pyridinyl)-4-[4-(3-pyridinyl)butyl]piperazine

A solution of 1-(3-pyridinyl)-4-[4-(2-pyridinyl)-1-piperazinyl]-1-butanone (Example 2) (5.2 g, 0.0168 mol), hydrazine hydrate (1.9 g, 0.0603 mol), and potassium hydroxide (3 g, 0.0538 mol) in ethylene glycol (100 mL) is refluxed 12 hours removing the water formed with a Dean-Stark trap. The cooled reaction mixture is diluted with water (100 mL) and extracted with dichloromethane. The organic layer is dried (sodium sulfate) and the solvent evaporate in vacuo. The resulting residue is crystallized from 2-propanol and diethyl ether to give 2 g of 1-(2-pyridinyl)-4-[4-(3-pyridinyl)butyl]piperazine as a white solid; mp 54–64° C.

In a process analogous to Example 8 using appropriate starting materials the corresponding compounds of Formula I (Examples 9 to 13) are prepared as follows:

EXAMPLE 9

2-4-[4-(4-Pyridinyl)butyl]-1-piperazinyl]pyridine mp 56-58° C.

EXAMPLE 10

2-[4-[4-(4-Pyridinyl)butyl]-1-piperazinyl]pyrimidine mp 49° C.

EXAMPLE 11

3-[4-[4-(2-Pyridinyl-1-piperazinyl]butyl]quinoline mp 89-90° C.

EXAMPLE 12

3-[4-[4-(2-Pyrimidinyl)-1-piperazinyl]butyl]quinoline mp 70-71° C.

EXAMPLE 13

4-[4-[4-(2-Pyridinyl)-1-piperazinyl]butyl]quinoline mp 70-71° C.

PREPARATION OF STARTING MATERIALS

EXAMPLE A

3-Pyridinylpropylchloride

A solution of 3-(3-pyridinyl)-1-propanol in concentrated hydrochloric acid (60 mL) is refluxed for 12 hours. The solution is made basic with sodium hydroxide and extracted with dichloromethane. The organic layer is dried (sodium sulfate) and the solvent is evaporated in vacuo to give 11.3 g of 3-pyridinylpropylchloride.

EXAMPLE B

4-Chloro-1-(3-pyridinyl)-1-butanone (Sato, M., et al, *Chem. Pharm. Bull.*, 26, 3296 (1978)).

A solution of methyl nicotinate (59 g, 0.43 mol), 4-hydroxybutyric acid lactone (51.8 g, 0.602 mol), and sodium methoxide (70 g, 1.29 mol) in dioxane (500 mL) is refluxed for 1 hour and then cooled. Concentrated hydrochloric acid (650 mL) is added, and the reaction mixture refluxed for 12 hours. The resulting solution is neutralized with solid sodium bicarbonate and extracted with chloroform. The organic phase is dried (sodium sulfate), and the solvent evaporated in vacuo. The residue is taken up in 2-propanol (50 mL) and treated with a saturated solution of hydrogen chloride in 2-propanol. The hydrochloride salt of 4-chloro-1-(3-pyridinyl)-1-butanone is obtained as a white solid (30 g); mp 73-76° C.

We claim:

1. A compound of Formula I

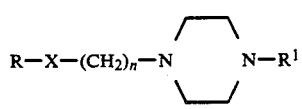

wherein R is

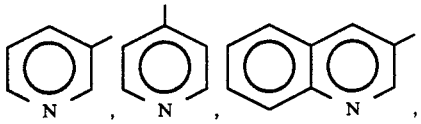

or

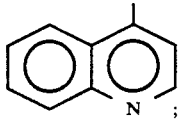

X is

or —CH$_2$—;

n is an integer of 2 to 4;

R$^1$ is 2- or 3-1H-indolyl, or 2- or 3-1H-indolyl substituted by lower alkyl, lower alkoxy, or halogen, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl, or 2- or 3-thienyl substituted by lower alkyl or halogen, 2- or 3-furanyl, or 2- or 3-furanyl substituted by lower alkyl or halogen, 2-, 4-, or 5-thiazolyl, or 2-, 4-, or 5-thiazolyl substituted by lower alkyl or halogen; or a pharmaceutically acceptable acid addition salt thereof with the exclusion of a compound where R is

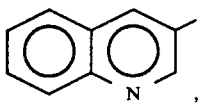

or

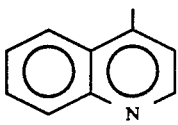

and X is CH₂.

2. A compound according to claim 1, in which R¹ is 2- or 3-1H-indolyl, or 2- or 3-1H-indolyl substituted by lower alkyl, lower alkoxy, or halogen, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2- or 3-thienyl or 2- or 3-thienyl substituted by lower alkyl or halogen.

3. A compound according to claim 2, in which R¹ is 2- or 3-1H-indolyl, 2-, 3-, or 4-pyridinyl, 2-, 4-, or 5-pyrimidinyl, or 2- or 3-thienyl.

4. A compound according to claim 3 selected from the group consisting of:

1-(3-Pyridinyl)-4-[4-(2-pyridinyl)-1-(piperazinyl)]-1-butanone;
1-(2-Pyridinyl)-4-[4-(3-pyridinyl)butyl]piperazine;
1-(4-Pyridinyl)-4-[4-(2-pyridinyl)-1-piperazinyl]-1-butanone;
2-[4-[4-(4-Pyridinyl)butyl]-1-piperazinyl]pyridine;
2-[4-[4-(4-Pyridinyl)butyl]-1-piperazinyl]pyrimidine;
1-(2-Pyridinyl)-4-[3-(3-pyridinyl)propyl]piperazine;
1-(3-Quinolinyl)-4-[4-(2-pyridinyl)-1-(piperazinyl)]-1-butanone;
1-(4-Quinolinyl)-4-[4-(2-pyridinyl)-1-piperazinyl]-1-butanone;
1-(3-Pyridinyl)-4-[4-(2-pyrimidinyl)-1-piperazinyl]-1-butanone; and
1-(4-Pyridinyl)-4-[4-(2-pyrimidinyl)-1-piperazinyl]-1-butanone.

5. A method of treating schizophrenia comprising administering to a host suffering therefrom a therapeutic effective amount of a compound according to claim 1 in unit dosage form.

6. A method of treating depression comprising administering to a host suffering therefrom a therapeutic effective amount of a compound according to claim 1 in unit dosage form.

7. A pharmaceutical composition adapted for administration as a dopaminergic, antipsychotic, antihypertensive or antidepressant agent comprising a therapeutic effective amount of a compound according to claim 1 in admixture with a pharmaceutically acceptable excipient, diluent or carrier.

* * * * *